United States Patent [19]
Di Sario

[11] Patent Number: 5,769,636
[45] Date of Patent: Jun. 23, 1998

[54] SYSTEM FOR DIAGNOSIS, PLACEMENT AND PROSTHETIC RESTORATION OF ROOT FORM IMPLANT

[76] Inventor: Francesco Di Sario, V. Garibaldi 29, Canosa Sannita, 66010, Italy

[21] Appl. No.: 698,886

[22] Filed: Aug. 16, 1996

[51] Int. Cl.$^6$ .............................. A61C 11/00; A61C 3/00
[52] U.S. Cl. ............................................ 433/213; 433/75
[58] Field of Search ................. 433/72, 75, 76, 433/213; 33/513, 514

[56] References Cited

U.S. PATENT DOCUMENTS

| | | | |
|---|---|---|---|
| 4,762,491 | 8/1988 | Bolton | 33/514 |
| 5,015,183 | 5/1991 | Fenick | 433/76 |
| 5,176,516 | 1/1993 | Koizumi | 433/72 |
| 5,320,529 | 6/1994 | Pompa | 433/76 |
| 5,556,278 | 9/1996 | Meitner | 433/75 |

FOREIGN PATENT DOCUMENTS

| | | | |
|---|---|---|---|
| 2716961 | 10/1978 | Germany | 433/72 |
| 9426200 | 11/1994 | WIPO | 433/75 |

*Primary Examiner*—Cary E. O'Connor
*Attorney, Agent, or Firm*—Gottlieb, Rackman & Reisman, P.C.

[57] ABSTRACT

A method and system for optimally positioning a tooth implant in the alveolar ridge of the patient's mouth is provided. A lateral plane of inclination is first defined that is cosmetically consistent with the lateral inclination of the teeth adjacent the area in the alveolar ridge where the implant is to be placed and which does not otherwise interfere with the roots of these teeth. Bone dimension in the alveolar ridge location where the implant is to be received is then determined. Finally, an anterior/posterior inclination is selected which is consistent with the anterior/posterior inclination of those same adjacent teeth. The dental implant is now capable of being guided to the implant site along the angular inclinations that were determined by the practitioner to be optimal.

40 Claims, 6 Drawing Sheets

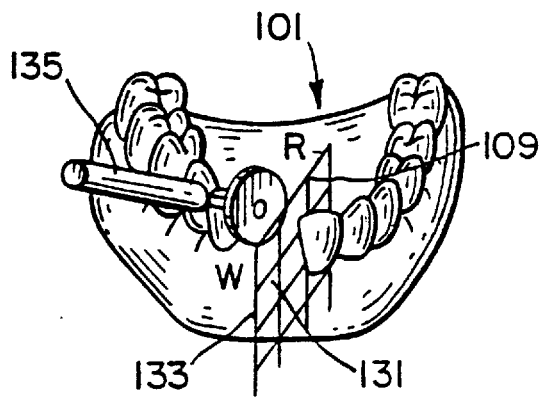
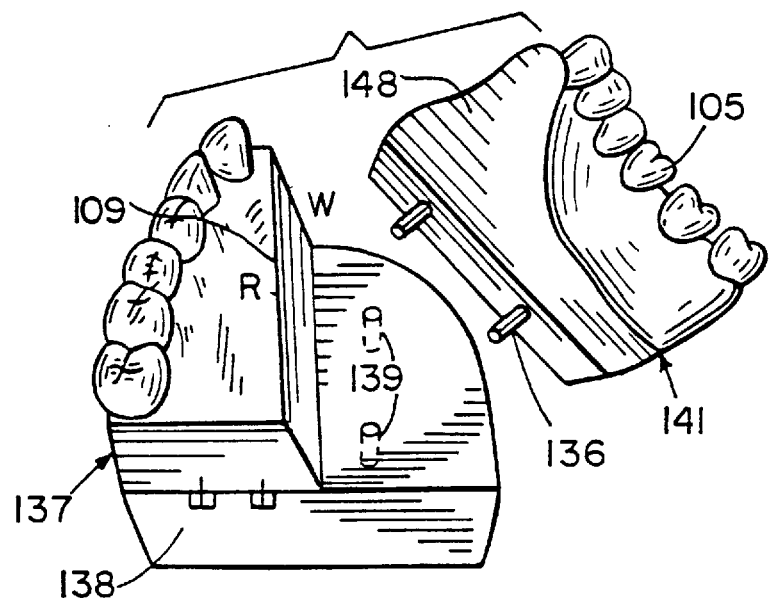
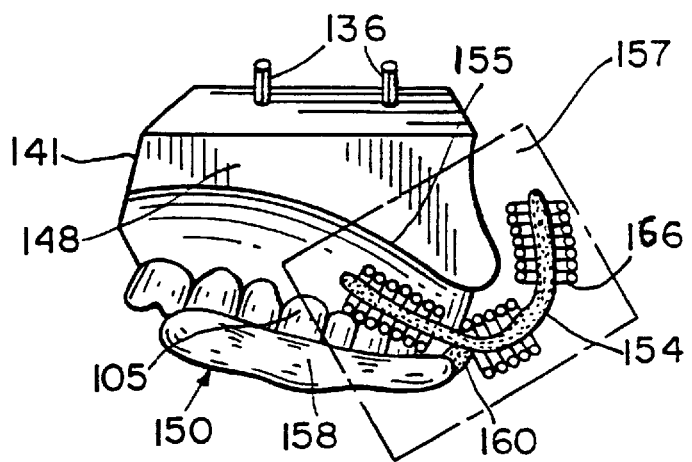

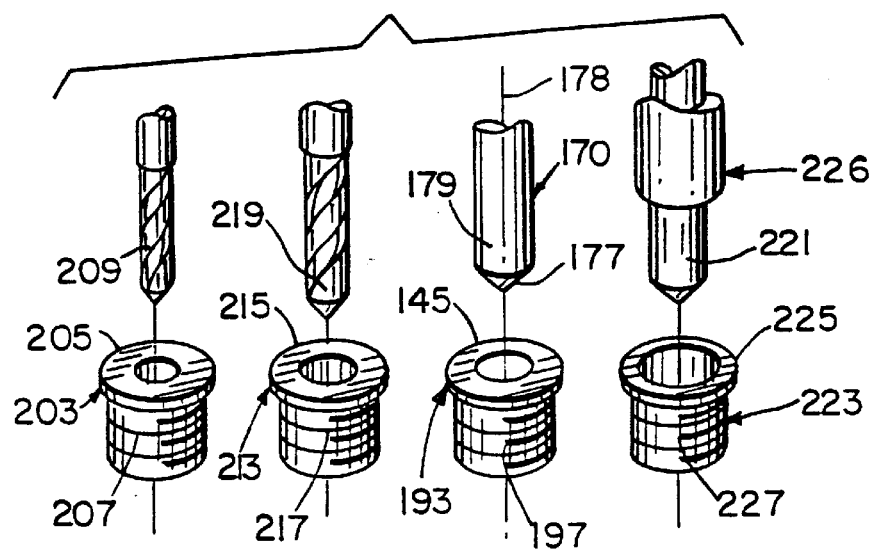
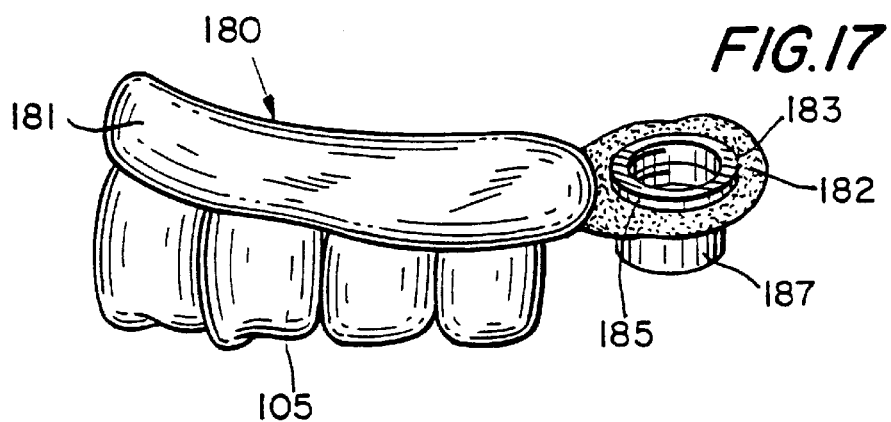
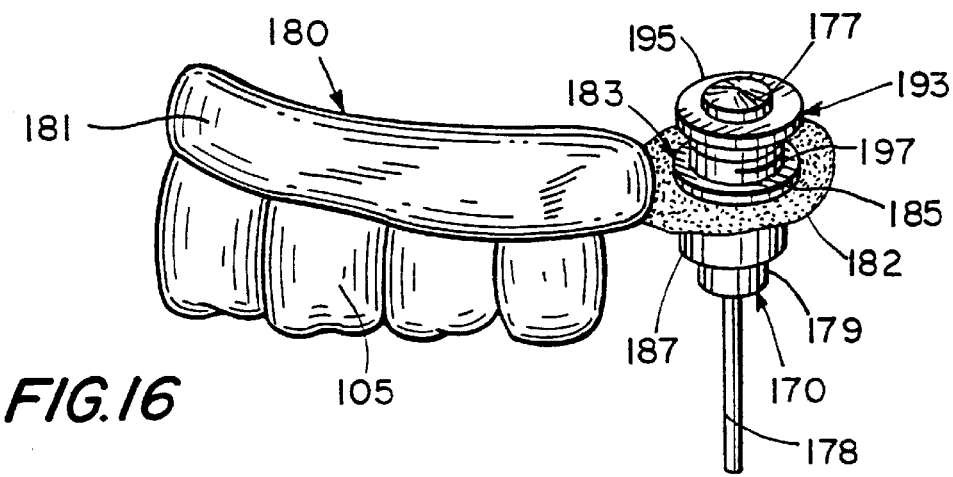

5,769,636

SYSTEM FOR DIAGNOSIS, PLACEMENT AND PROSTHETIC RESTORATION OF ROOT FORM IMPLANT

BACKGROUND OF THE INVENTION

This invention relates to a system and method for accurately positioning a tooth implant in one of a patient's upper or lower alveolar ridge(s).

There are several modalities for implant placement. Different kinds of surgical guides have been proposed in order to enable the surgeon to place an implant in a patient's mouth in a manner which facilitates restorative therapy, within normal anatomic limitations and bone dimension. Nevertheless, most of the time such surgical guides are not used to dictate the final position of the implant, in large part because during guide fabrication, bone and soft tissue dimensions were not considered.

One system that has been identified in the literature is "computer-assisted tomography," which is a somewhat predictable way for a dental practitioner to determine the position of the bone and thereby fabricate an appropriate surgical guide. However, this type of technique provides a virtual image with a range of distortion that is not easily predictable; moreover, the patient is exposed to a great deal of radiation when this procedure is carried out. Finally, the quality of the image is less than desirable due to inadvertent movement of a patient during the scanning process.

Accordingly, it would be desirable to provide a dental implant procedure which overcomes these disadvantages.

SUMMARY OF THE INVENTION

Generally speaking, in accordance with the invention, a method and system for optimally positioning a tooth implant in a patient's mouth is provided. The first step in the method comprises defining a lateral plane of inclination with respect to the chosen alveolar ridge such that the lateral inclination angle is aesthetically consistent with the lateral inclination of the teeth adjacent to the area where the implant is to be placed and properly positioned with respect to the roots thereof.

After this lateral inclination plane is determined, the next step in the inventive method is to determine the bone dimension in the location where the implant is to be placed. Once this is achieved, it is necessary to then define an anterior/posterior inclination for the implant to be positioned, such that said inclination is aesthetically consistent with the posterior/anterior inclination of the teeth adjacent to where the implant is to be placed. Finally, using specially designed dental surgical guides, a hole is drilled in the alveolar ridge, and the desired dental implant is fixed therein by directing the implant thereto along the angular inclinations that were determined by the dental practitioner to be optimal.

In order to determine the appropriate lateral plane of inclination, a specially designed dental tool is used which can effectively simulate the desired lateral inclination of the implant. Once the desired lateral inclination is selected and recorded using this tool, a specially designed radiographic stent is prepared which is then used to verify the suitability of this lateral inclination as it relates to the roots of the adjacent teeth. If the lateral inclination is found to be satisfactory, it is marked on a stone cast impression of the patient's mouth and the cast is then sectioned in order to define a planar surface consistent with the chosen lateral inclination.

In order to determine the thickness of the bone in the patient's mouth where the implant is to be placed, a second specially designed dental stent is fabricated. Utilizing one or more specially designed probes, the location of the patient's alveolar bone can be reproduced without soft tissue distortion and marked on the sectioned stone cast.

The anterior/posterior inclination is determined by using a specially designed pin which is fixed on the sectioned dental cast along the planar surface in a direction which reflects the desired anterior/posterior inclination for placing the tooth implant in the alveolar ridge. A third surgical dental stent is then prepared utilizing the angular orientation of the pin. The stent, in conjunction with a metal ring fixed thereto, is used to guide placement of the dental implant in the alveolar ridge by directing the implant to the selected site in the ridge along the angular inclinations that were calculated by carrying out the inventive technique.

Accordingly, it is an object of the invention to provide an improved method and system to accurately and reproducibly direct the positioning of a tooth implant in a patient's upper or lower alveolar ridge.

Still another object of the invention is to provide specially designed dental stents that are used in determining implant orientation in the alveolar ridge.

A further object of the invention is to provide specially designed tools for carrying out the inventive procedure.

Still other objects and advantages of the invention will in part be obvious, and will in part be apparent, from the following description.

The invention accordingly comprises the several steps and the relation of one or more such steps with respect to each of others, and the system defined by the elements and arrangement of parts which are adapted to effect such steps, all as exemplified in the following detailed disclosure, and the scope of the invention is indicated in the claims.

BRIEF DESCRIPTION OF THE DRAWINGS

For a fuller understanding of the invention, reference is made to the following description, taken in conjunction with the accompanying drawings, in which:

FIG. 7 is a front elevational view which shows cutting of the dental cast in accordance with the plane of lateral inclination that was previously determined;

FIG. 8 is an exploded perspective view showing the dental cast of FIG. 7 after it has been cut, divided into two parts and then selectively mounted on a plaster base;

FIG. 9 is a perspective view of one of the cast parts shown in FIG. 8 and the manufacture of a specially designed second dental stent thereon for use with a series of tubes disposed about a common plane to the planar surface of the cast part;

FIG. 15 is an exploded view showing various size guide rings and parts of surgical instruments used therewith for carrying out the inventive process;

FIG. 16 is a perspective view showing use of one of the guide rings in preparing a third specially designed dental stent along the cast part;

FIG. 17 is a perspective view showing the third dental stent in a completed condition along the teeth of the cast part.

DETAILED DESCRIPTION OF THE DRAWINGS

Initially, a stone cast, generally indicated at 101, is prepared by pouring an impression of the mouth of the patient. In preparing stone cast 101, a stable and accurate impression material is used that is well known in the art. The impression material is poured with a die stone as is also known in the art.

Figure 1:
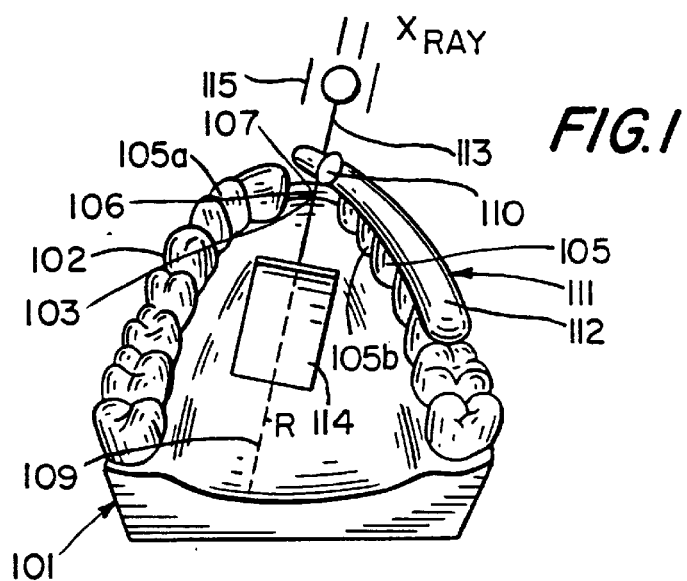
FIG. 1 is a perspective view illustrating the fabrication along a dental cast of a first dental stent for use in determining a desired plane of lateral inclination and its verification of suitability by radiograph for the inventive technique.

Referring now to FIG. 1, the dental practitioner draws a curved line 103 between teeth 105*a* and 105*b* of cast 101 in order to reproduce the shape of the dental arch 102 in the area or location along cast 101 where a missing tooth is to be replaced. Once curved line 103 is drawn along cast 101, a point or position 107 along line 103 is selected for specific placement of the implant. Position 107 is usually the location along line 103 that is equidistant between teeth 105*a* and 105*b*.

Thereafter, the practitioner draws a straight line 109(R) which passes through position 107 and which is also orthoradially directed through curved line 103, as shown. As can be appreciated, straight line 109(R) is substantially perpendicular to tangent line 106 of line 103. Straight line 109 will later be used in determining the plane of lateral inclination for placement of the implant in the alveolar ridge of the patient's mouth, as well as guiding the direction of X-ray beams in confirming the lateral indication that was determined, as described below.

Continuing with FIG. 1, a radiographic stent 111 is fabricated along teeth 105 of stone cast 101. In general, a stent is an acrylic device that is fabricated on the teeth of stone cast 101 and is transferable to the mouth of the patient along the corresponding teeth thereof. A dental stent is capable of reproducing the exact location of any element fixed thereto with respect to the stone cast of the mouth or the actual mouth of the patient. In effect, the stent functions like a "shuttle," carrying information relating to position between the stone cast and the mouth without any distortion or discrepancy.

Significantly, the stents used in the inventive system are supported or carried along the teeth of either the stone cast or those in the patient's mouth, and not along any soft dental tissue, such as the gum. The latter typically exhibits significant elasticity and compressibility, precluding accurate reproducibility of element location with respect to the placement thereof along the cast or in the patient's mouth. If a patient does not have any teeth, an implant system can be used to support the stents in order to carry out the inventive technique.

Radiographic stent 111 includes a frame 112, which is made from a lightly cured resin material as is well known. Stent 111 is connected to a film holder 113 by means of an auto-polymerizable resin 110. As shown in FIG. 1, film holder 113 retains a standard X-ray film 114 that is to be oriented perpendicularly to line 109(R) (which guides the direction of X-ray beam 115), as described hereinafter.

Figure 2:
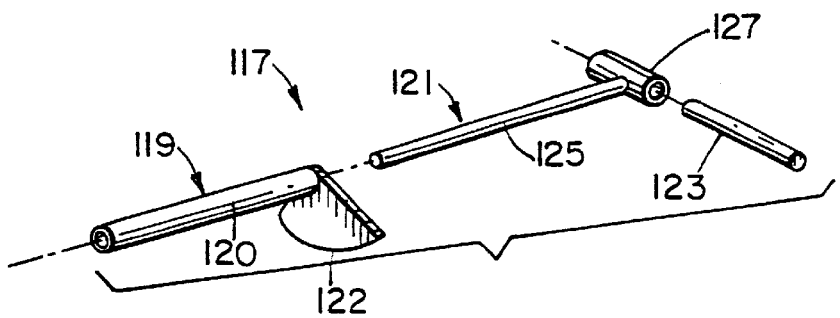
FIG. 2 is an exploded perspective view of a tool assembly of the inventive procedure that is used in determining the desired plane of lateral inclination.

Once radiographic stent 111 has been fabricated, it is temporarily removed from cast 101. Then, the plane of lateral (mesio distal) inclination for placement of the dental implant is determined using a specially designed dental tool assembly generally indicated at 117, as illustrated in FIG. 2.

Tool assembly 117 comprises a tube member 119, a T member 121 that is removably insertable inside tube 119, and an arm 123. Each of these elements of tool 117 is made of stainless steel or some other material which has the characteristics of rigidity, dimensional stability, resistance to fracture, biocompatibility, non-corrosiveness and resistance to sterilization methods. These characteristics are also applicable for any of the other tools or devices that are used in the inventive technique.

Figure 3:
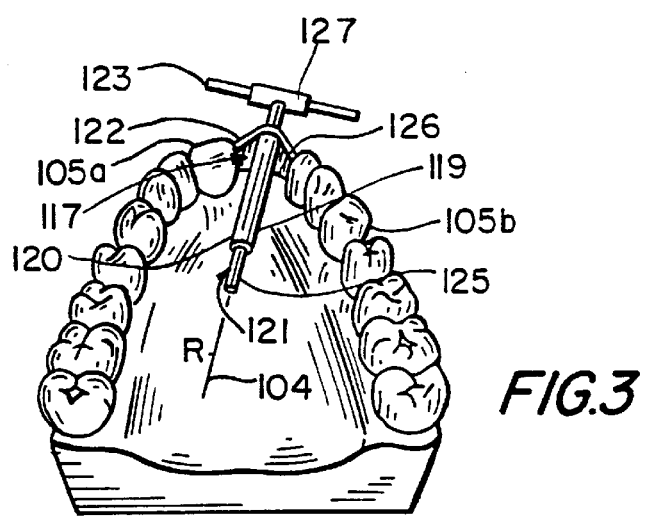
FIG. 3 is a perspective view similar to FIG. 1 and illustrating use of the tool assembly shown in FIG. 2 in conjunction with the dental cast depicted in FIG. 1.

Tube member 119 comprises a tube 120 to which a fin 122 is fixed at a right angle at one end thereof, as shown. T member 121 of tool assembly 117 comprises an extending post 125 that is connected at a substantial right angle with a second tube 127. In assembly with tube member 119, post 125 slides within tube 120, as shown in FIG. 3. In addition, arm 123 slides into tube 127 of T member 121.

Referring now to FIG. 3, tube member 119 is first fixed in place on cast 101 by placing fin 122 along ridge 126 located between teeth 105*a* and 105*b* such that tube 120 is substantially aligned with straight line 109(R). Then, T member 121 is coupled to tube member 119 by slipping post 125 inside of tube 120, as shown. Thereafter, arm 123 is inserted within tube 127 of T member 121, the latter which freely rotates within tube member 119. Arm 123 can now be used to simulate the desired lateral inclination of the implant; it may be moved or rotated laterally by the dental practitioner until an ideal inclination is achieved.

Figure 4:
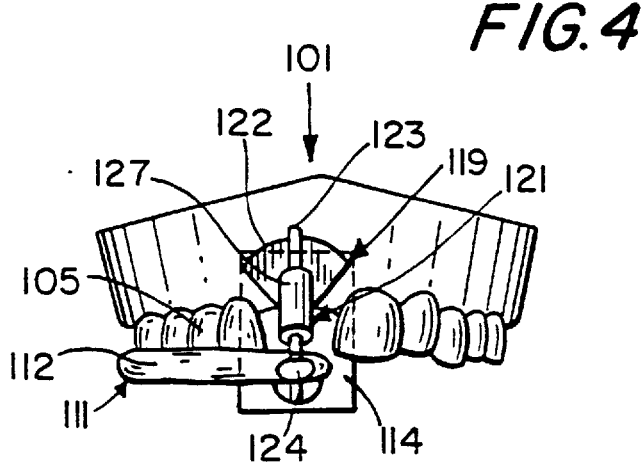
FIG. 4 is a front elevational view showing how the tool assembly depicted in FIG. 2 is used to select a desired plane of lateral inclination in preparing the first dental stent along the dental cast.
Figure 5:
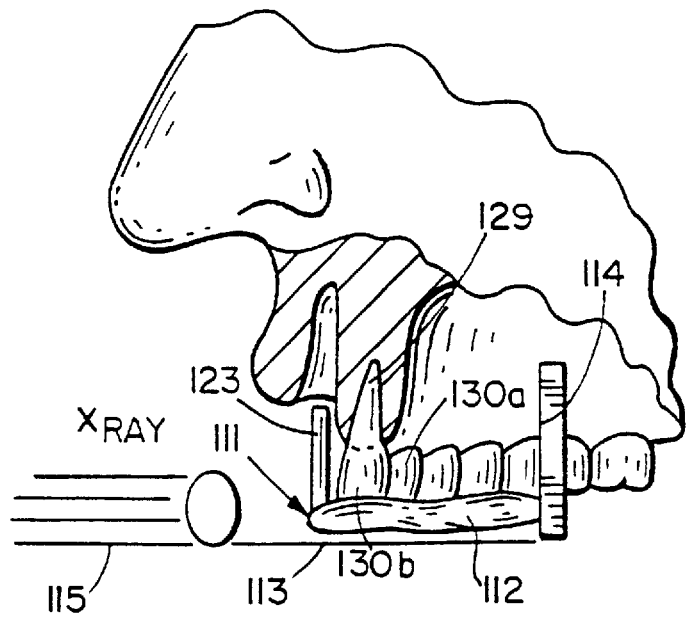
FIG. 5 is a side elevational view illustrating appropriate transfer of the dental stent prepared in FIG. 4 to a patient's mouth.

As shown in FIG. 4, arm 123 of tool assembly 117 is now attached to radiographic stent 111 that was previously fabricated (see FIG. 1). In particular, after selectively rotating arm 123 to an appropriate lateral inclination, stent 111 is fixed to arm 123 by means of an applied resin material 124. After removing arm 123 from tube 127 of T member 121, stent 111 and attached arm 123 are together transferred to the mouth of the patient (see FIG. 5); there, an X-ray is taken by the practitioner of the front portion of the mouth.

Figure 6:
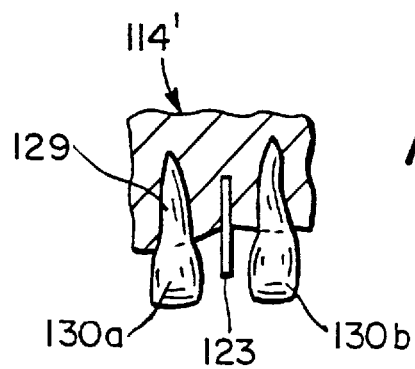
FIG. 6 is a front planar view of an X-ray picture that was taken from the set-up in FIG. 5.

The X-ray of the mouth will enable the dental practitioner to verify the suitability of the lateral inclination that was chosen. As illustrated in FIG. 6, the developed film 114' from the X-ray procedure depicts the position of arm 123 within the implant location, and its relationship to the position of roots 129 of teeth 130a and 130b (which correspond to cast teeth 105a and 105b).

After X-ray film 114' is evaluated, if the proposed lateral inclination of the implant is found to be satisfactory by the dental practitioner, the practitioner then takes radiographic stent 111 (with attached arm 123) and places it back on stone cast 101, guiding the sectioning thereof, as described below. If the proposed lateral inclination of the implant is not considered to be satisfactory by the dental practitioner, the practitioner will adjust the inclination of arm 123 on the radiographic stent, after which its position is checked once again by taking another X-ray of the patient's mouth.

Once the lateral inclination selected is considered satisfactory, it is then necessary to determine the cross-sectional plane that will be used for placing the implant in its proper lateral inclination within the patient's mouth. As shown in FIG. 7, this plane is determined to be defined by the straight line 109 (R) (previously recorded) and an inclination line 133 (W) defined by arm 123. This defined plane, generally indicated at 131, is marked on stone cast 101 and then cast 101 is sectioned according to these geometric coordinates.

Before sectioning, cast 101 is mounted on a dental plaster system (for example, a Pindex™ system), as is well known in the art (see FIG. 8). The Pindex™ system allows the practitioner to connect stone cast 101 to a base of plaster 138 by means of tubes 139, which selectively receive corresponding pins 136 located along the underside of cast 101, as depicted in FIG. 9. Cast 101 is then sectioned by means of a hand or mechanical saw 135, or some other well known tool (see FIG. 7). Once cast 101 has been sectioned, it now defines two parts, 137 and 141, each of which can be selectively removed from plaster base 138 and subsequently placed back thereon by means of pins 136 and tubes 139. As best shown in FIG. 8, cast part 141 includes a lateral planar surface 148 that was formed when sectioning cast 101 along plane 131, as described above.

Turning to FIGS. 9–12, the second step in the inventive technique, namely determining the position of the alveolar bone, is now illustrated. As with the process of determining the plane of lateral inclination of the implant, stone cast 101, and in particular, cast part 141 is used.

Initially, a bone measuring stent generally indicated at 150 is fabricated. As depicted in FIG. 9, a series of metal tubes 166 are first configured together. Each of tubes 166 preferably has a smooth internal wall and a roughened external surface, the latter in order to facilitate fixation within resin 154.

Tubes 166 are positioned so that they are disposed along the same cross-sectional plane as that of planar surface 148. This is achieved by using an acetate template (a transparent foil) 157 (see FIG. 9), which is placed on planar surface 148 of cast part 141. Then the practitioner, using a pencil or some other marking tool, records a border 155 of surface 148 on template 157.

After first removing template 157 from cast part 141, tubes 166 are placed along template 157 and around border 155, and are configured together in this position utilizing an autopolymerizing resin 154. Then, tubes 166, now appropriately configured together, are, with template 157, placed on cast part 141 so that border 155 lines up with the actual border of cast part 141 (see FIG. 9).

Stent 150 is now fabricated along teeth 105 of cast part 141 in order to create a stent frame 158. With tubes 166 positioned appropriately in the same cross-sectional plane, stent 150 is attached to the series of tubes 166 by additional autopolymerizing resin 160. Template 157 may now be removed.

Figure 10:
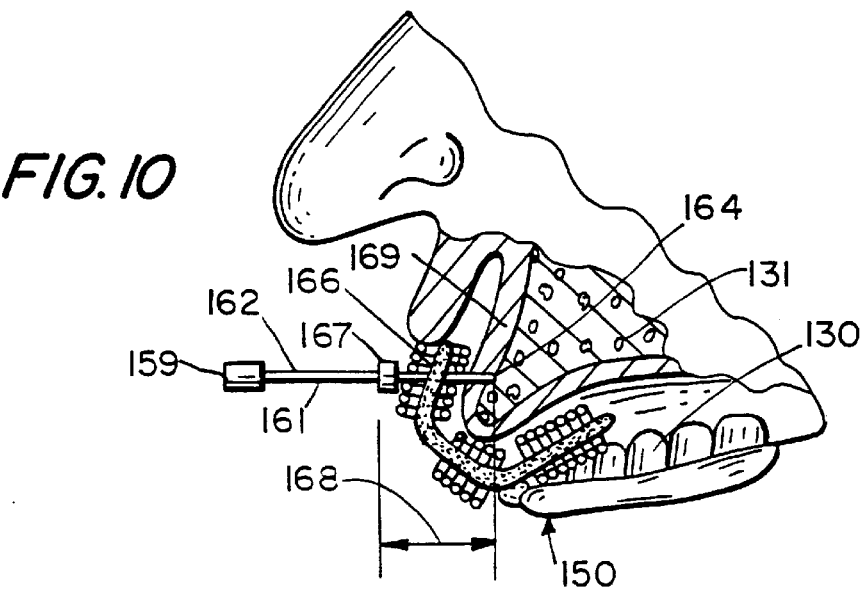
FIG. 10 is a side elevational view showing use of the second dental stent shown in FIG. 9 in measuring alveolar bone location in the patient's mouth.

Once stent 150 (with attached tubes 166) has been fabricated along cast part 141, it is then transferred to the patient's mouth so that the position of bone 131 may be accurately located. Referring now to FIG. 10, utilizing one or more metal probes 162, the distance 168 between bone surface 164 and tubes 166 fixed to stent 150 is measured. Each metal probe has a handle 159 and an extending non-tapered rigid shank 161 leading to a tip 163. Handle 159 may include a hole for receiving a wire (not shown)—this wire is used to remove probe 162 if it inadvertently falls down the throat of the patient. In use, probe 162 is slidably inserted into and through metal tubes 166 (see FIG. 11). Significantly, shank 161 of probe 162 is rigid and smooth surfaced, facilitating insertion through tubes 166.

Figure 11:
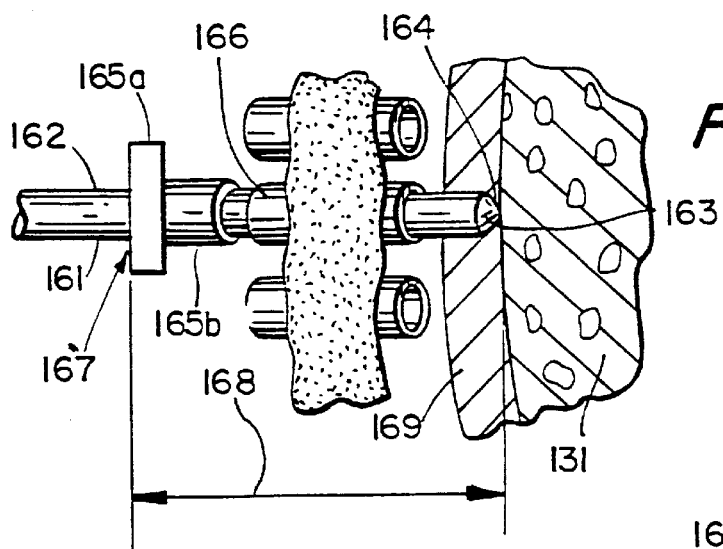
FIG. 11 is an enlarged view of a portion of FIG. 10, and illustrates use of a metal probe and stop member in measuring alveolar bone location.

Tip 163 of shank 161 is pointed, as best shown in FIG. 11, so that it easily passes through the dental soft tissue (gum) when shank 161 of probe 162 is inserted through tubes 166. Obviously, tip 163 of shank 161 stops when it hits or otherwise contacts the alveolar bone.

A stop member 167, slidably situated along shank 161 of each probe 162, is then used to calculate the distance between bone surface 164 and stent 150. Stop member 167 comprises an elastic ring 165a and a tube 165b disposed about shank 161 of probe 162 and projecting longitudinally toward tip 163 thereof (see FIG. 11). Tube 165b of stop member 167 is used to record distance 168 between surface 164 and stent 150, as now described.

Once probe 162 is inserted through one of tubes 166, such that tip 163 of shank 161 contacts the alveolar bone, the dental practitioner slides stop member 167 until tube 165b abuts tube 166 (fixed in position to stent 150). This probing process is repeated with respect to each of tubes 166.

Figure 12:
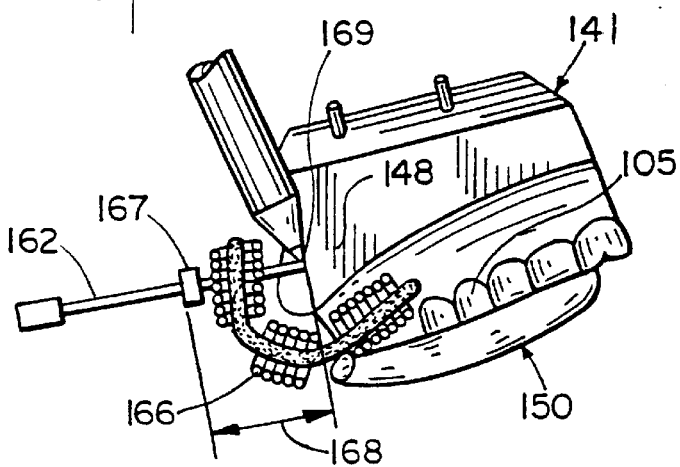
FIG. 12 is a perspective view illustrating the marking by the dental practitioner of the cast part depicted in FIG. 9 in order to record the location thereon of the dental bone.

Once probing is completed, stent 150 is placed back on stone cast part 141 (see FIG. 12). Then, the distances 168 between bone surface 164 and stent 150, as calculated above during the probing process, are marked on planar surface 148 of cast part 141 in order to record the exact position of the bone thereon. In other words, each probe 162 is used to select a location 169 along planar surface 148 where probe 162 had abutted against bone surface 164 in the patient's mouth. The location of bone 131 (independent of the position of gum or soft tissue 169, but dependent upon stent 150 as it is seated on teeth 130) of the patient is now accurately recorded on stone cast part 141.

Figure 13:
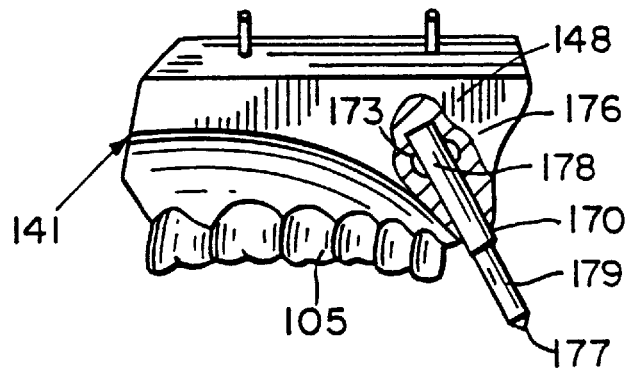
FIG. 13 is a perspective view of a specially designed pin member mounted along the lateral planar surface of the cast part for selecting a desired anterior/posterior inclination to be used during the dental implantation.

Turning now to FIG. 13, calculation of the anterior/posterior (buccolingual) inclination that is to be used for the implant procedure is now described. This is achieved by utilizing a metallic pin member 170 which comprises a rectangular substantially flat configured magnetically attractable shank 178 and a lower cylindrical body 179 leading to a pointed tip 177. Shank 178 of pin member 170 has a substantially smooth surface and is made from a magnetically attractable metal or alloy material. Body 179 of pin member 170 is either hollow or solid and has a polished surface. As shown in FIG. 13, pin member 170 is fixed on cast part 141 by slidably mounting shank 178 thereof along lateral surface 148, as described below.

Figure 14:
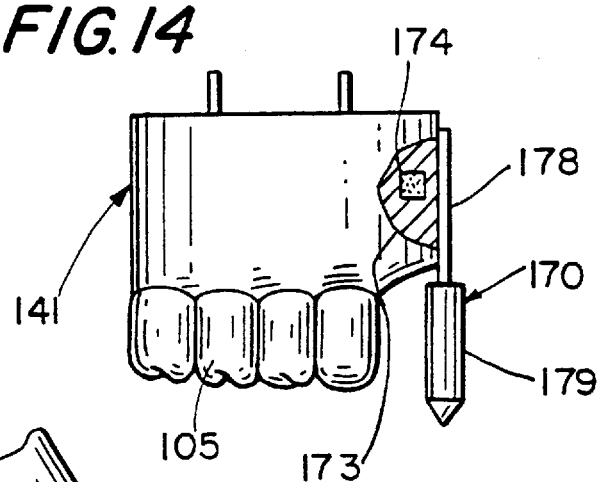
FIG. 14 describes the placement of a magnet within the cast part so that the pin member may be rotatably adjusted along the lateral planar surface thereof when selecting a desired anterior/posterior inclination for positioning of the implant.

Referring now also to FIG. 14, in order to mount pin member 170 along lateral surface 148 of cast part 141, a magnet 174 is incorporated within cast part 141. This is achieved by excavating a small hole 173 underlying lateral surface 148 of cast part 141 and at a location 176 well within what was previously marked as identifying where the alveolar bone would be situated. Then, magnet 174 is incorporated in hole 173 by utilizing a conventional gluing material. Once this is achieved, pin member 170 is slid along lateral surface 148 of cast part 141 so that magnetically attractable shank 178 lies over hole 173 in which magnet 174 has been placed. If hole 173 has been prepared correctly, shank 178 of pin member 170 does not actually contact magnet 174, as magnet 174 is situated slightly below surface 148—consequently, rotational movement of pin member 170 is not hindered.

At this juncture, the dental practitioner can adjustably rotate pin member 170 about the upper end of shank 178 (see FIG. 13) so that an anterior/posterior position is achieved that the practitioner considers cosmetically desirable. Once a final position is determined, a third surgical stent is then fabricated, as described below.

Referring now to FIGS. 15 and 16, preparation of surgical stent 180 is now described. Surgical stent 180 is made of an acrylic frame 181 to which a metallic ring generally indicated at 183 is fixed. Ring 183 comprises an annular shoulder 185 and a tubular depending shank 187 (see also FIG. 17). Shank 187 is threaded internally for selectively receiving different sized guide rings and avoiding the inadvertent rotation thereof after reception, as described hereinafter.

In order to prepare surgical stent 180, a first metallic guide ring 193 is utilized (see FIG. 15). Guide ring 193 comprises an annular shoulder 195 and a depending shank 197. Shank 197 of ring 193 is threaded externally therealong, as shown, for selectively mating with shank 187 of ring 183. Shank 197 of ring 193 has an internal diameter which is sized for selectively receiving cylindrical body 179 of pin member 170 therethrough, as discussed later on.

Referring also now to FIG. 16, ring 193 is first threaded into and received within ring 183. With pin member 170 mounted along lateral surface 148 of cast part 141, as already selected by the practitioner, tip 177 of body 179 is fitted through shank 197 of guide ring 193. Then, ring 183 is fixed to frame 181 of stent 180 by an autopolymerizing resin 182 that is effectively wiped around shank 187 and just below shoulder 185. This process accurately and exactly fixes ring 183 on stent 180 such that ring 183 has an axis running longitudinally therethrough which defines the anterior/posterior and lateral inclinations that were selected (see FIG. 17).

Once ring 183 is fixed to stent 180, both ring 193 and pin member 170 are removed from ring 183—thus, only ring 183 remains attached to stent 180, as shown in FIG. 17. Surgical stent 180 is now capable of being transferred to the mouth of a patient, and, with ring 183 fixed in position thereto, is used as a surgical guide during the actual tooth implantation process, as now described.

Referring once again to FIG. 15, metallic guide rings 203 and 213 are also shown. Each of guide rings 203 and 213 comprises respectively an annular shoulder 205 and 215 and a depending shank 207 and 217. Shanks 207 and 217 of respective rings 203 and 213 are both externally threaded for selective reception within internally threaded shank 187 of ring 183 (now fixed in proper position to stent 180).

Rings 203 and 213 are used for guiding surgical drills 209 and 219 well known in the art, as shown. As can be appreciated, drill 209 has a smaller diameter or thickness than drill 219. Drill 209 is first used in order to drill out an implant site 220 (see FIG. 18) in the patient's alveolar ridge. This is achieved by running drill 209 through guide ring 203 (see FIG. 15) once the latter is threaded into and received within ring 183. Since stent 180 is now appropriately disposed in the patient's mouth, drill 209 is guided exactly to the location in the patient's alveolar ridge where the implant is to be placed in the desired lateral and anterior/posterior directions.

After drill 209 is used, ring 203 is removed from ring 183 and replaced with guide ring 213 in a similar manner as that previously described for ring 203. Then drill 219 (the drill with the larger diameter) is fed through guide ring 213 while the latter is received within ring 183 fixed to stent 180. As before, drill 219 is directed exactly to the location where the patient's implant is to be fixed and in the proper angular orientation. Drill 219, having a larger diameter than that of drill 209, facilitates enlargement of implant site 220 in the patient's alveolar ridge, and thus suitably prepares the implant site for reception of an actual dental implant 221.

Figure 18:
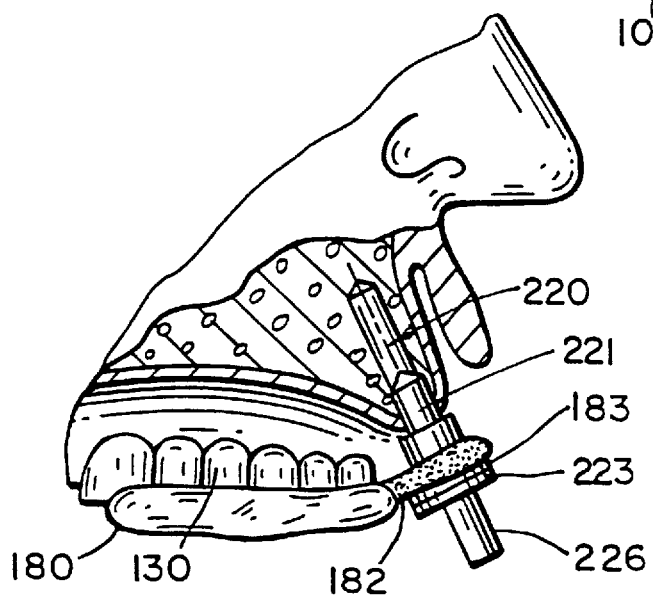
FIG. 18 is a side elevational view of a patient's mouth describing orientation and placement of the implant in the alveolar ridge utilizing the third specially designed dental stent.

Turning now to FIG. 18, delivery of dental implant 221 to dental implant site 220 in accordance with the invention is now described. This is achieved by utilizing guide ring 223 (see FIG. 15). Guide ring 223 has to be made from the same material (i.e., titanium) as implant 221. This is to avoid differing electric charges between ring 223 and implant 221 (galvanic phenomenon). Guide ring 223 comprises a head 225 and a depending shank 227. Shank 227 is externally threaded for selective engagement within internally threaded shank of ring 183 (fixed in proper position to stent 180).

Guide ring 223 is used for guiding placement of implant 221 in the patient's alveolar ridge. Implant 221 is carried by a mounting tool 226 known in the art, which is passed through guide ring 223 once the latter is threaded into and received within ring 183 (see FIG. 18). Mounting tool 226 is cylindrically configured. Since stent 180 is situated appropriately along teeth 130 in the patient's mouth, implant 221 is directed or guided to the implant site 220 with a specific angular orientation. This orientation (lateral and anterior/posterior inclinations) was that which was determined by the dental practitioner to be the most aesthetically and functionally desirable.

It will thus be seen that the objects set forth above, amount those made apparent from the preceding description, are efficiently attained and, since certain changes may be made in the above compositions, tools, techniques, and in the construction of the devices described, without departing from the spirit and scope of the invention, it is intended that all matter contained in the above description shall be interpreted as illustrative and not in a limiting sense.

It is also be to understood that the following claims are intended to cover all of the generic and specific features of the invention herein described and all statements of the scope of the invention which, as a matter of language, might be said to fall therebetween.

I claim:

1. A system for accurately positioning a tooth implant in an implant site located along the alveolar ridge of a patient's mouth comprising:

a dental impression cast of said mouth;

first means for defining an optimal plane of lateral inclination for placing said implant in said site in order to produce a planar surface of lateral inclination along said cast which reflects said defined optimal plane;

means for determining dental bone location in said alveolar ridge adjacent where said implant site is located in order to record said bone location on said planar surface of lateral inclination produced along said dental cast;

second means for defining an optimal anterior/posterior inclination along said planar surface of lateral inclination produced along said dental cast for placing said implant in said site; and means for directing placement of said tooth implant in said implant site based on 1) said anterior/posterior inclination defined along said planar surface of lateral inclination and 2) the recorded bone location on said planar surface.

2. The system of claim 1, wherein said first defining means includes means for simulating said plane of lateral inclination along said dental cast.

3. The system of claim 2, wherein said simulating means comprises means for identifying a line running along said cast orthoradially directed through the implant site thereon.

4. The system of claim 2, wherein said simulating means includes means for selective lateral rotation along said cast in order to select said desired angle of lateral inclination.

5. The system of claim 2, wherein said first defining means further includes a first dental stent for carrying and selectively transferring said simulating means in fixed position between said dental cast and said patient's mouth.

6. The system of claim 5, wherein said first dental stent includes means for verifying the suitability of said desired angle of lateral inclination when said fixed position lateral rotation means is carried by said first stent in said patient's mouth.

7. The system of claim 6, wherein said verifying means includes means for reproducing a radiographic picture of said fixed position lateral rotation means along said implant site when said rotation means is carried by said first stent in said patient's mouth.

8. The system of claim 1, wherein said determining means includes means for locating the dental bone in said alveolar ridge without being affected by any soft tissue distortion.

9. The system of claim 8, wherein said determining means further includes a second dental stent for carrying and selectively transferring said locating means in fixed position between said dental cast and said patient's mouth.

10. The system of claim 9, wherein said locating means comprises means for calculating along said defined optimal plane of lateral inclination the distance between said bone and said stent at various locations therealong.

11. The system of claim 10, wherein said calculating means includes means for marking said calculated distances on said planar surface of lateral inclination produced along said cast in order to record bone location thereon.

12. The system of claim 9, wherein said locating means includes a series of tubes fixed in position about said second stent and along said defined optimal plane of lateral inclination.

13. The system of claim 12, wherein said locating means further includes at least one probe for detecting the dental bone at various select locations by selectively passing at least one probe through said tubes.

14. The system of claim 1, wherein said second defining means comprises means for simulating a desired angle of anterior/posterior inclination along said planar surface of lateral inclination produced on said cast.

15. The system of claim 14, wherein said simulation means includes pin means selectively and rotatably fixed along said planar surface of lateral inclination of said cast.

16. The system of claim 15, wherein said pin means is selectively magnetically fixed to said planar surface of dental cast at one end of said pin means so that said pin means is selectively rotatable about said end.

17. The system of claim 15, wherein said pin means is rotatably fixed along said planar surface of lateral inclination where said bone location was recorded thereon.

18. The system of claim 1, wherein said placement directing means comprises guide means disposed along said defined optimal plane of lateral inclination in a direction reflecting the defined optimal anterior/posterior inclination.

19. The system of claim 18, wherein said placement directing means also includes a third dental stent for carrying and selectively transferring said disposed guide means in fixed position between said dental cast and the patient's mouth.

20. The system of claim 19, wherein said guide means selectively receives a drill means therethrough for directing said drill means to the implant site when said guide means, carried by said third stent, is in said patient's mouth.

21. The system of claim 19, wherein said guide means selectively receives therethrough means for delivering said implant to the implant site when said guide means, carried by said third stent, is in said patient's mouth.

22. A method for accurately positioning a tooth implant in an implant site located along the alveolar ridge of a patient's mouth comprising:

producing a dental impression cast of said mouth;

defining an optimal plane of lateral inclination for placing said implant in said site in order to produce a planar surface of lateral inclination along said cast which reflects the defined plane by simulating said plane of lateral inclination along said dental cast;

determining dental bone location in said alveolar ridge adjacent where said implant site is located in order to record said bone location on said planar surface of lateral inclination produced along said dental cast;

defining an optimal anterior/posterior inclination along said planar surface of lateral inclination produced along said dental cast for placing said implant in said site; and directing placement of said tooth implant in said implant site based on 1) said anterior/posterior inclination defined along said planar surface of lateral inclination and 2) the recorded bone location on said planar surface.

23. The method of claim 22, wherein said simulating step comprises identifying a line running along said cast orthoradially directed through the implant site thereon.

24. The method of claim 22, wherein said simulating step includes laterally rotating a marking pin along said cast in order to select said desired angle of lateral inclination.

25. The method of claim 24, wherein said first defining step further includes fabricating a first dental stent for carrying and selectively transferring said pin in fixed position between said dental cast and said patient's mouth once said desired angle of lateral rotation is selected.

26. The method of claim 25, wherein said first defining step further includes the step of verifying the suitability of said desired angle of lateral inclination when said fixed position pin is carried by said first stent in said patient's mouth.

27. The method of claim 26, wherein said verifying step comprises reproducing a radiographic picture of said fixed position pin along said implant site when said pin is carried by said first stent in said patient's mouth.

28. A method for accurately positioning a tooth implant in an implant site located along the alveolar ridge of a patient's mouth comprising:

producing a dental impression cast of said mouth;

defining an optimal plane of lateral inclination for placing said implant in said site in order to produce a planar surface of lateral inclination along said cast which reflects the defined plane;

determining dental bone location in said alveolar ridge adjacent where said implant site is located in order to record said bone location on said planar surface of lateral inclination produced along said dental cast by locating the dental bone in said alveolar ridge without being affected by any soft tissue distortion;

defining an optimal anterior/posterior inclination along said planar surface of lateral inclination produced along said dental cast for placing said implant in said site; and directing placement of said tooth implant in said implant site based on 1) said anterior/posterior inclination defined along said planar surface of lateral inclination and 2) the recorded bone location on said planar surface.

29. The method of claim 28, wherein said locating step comprises the step of calculating along said defined optimal plane of lateral inclination the distance between the bone and said second dental stent at various locations therealong.

30. The method of claim 29, wherein said calculating step comprises marking said calculated distances on said planar surface of lateral inclination produced along said cast in order to record bone location thereon.

31. The method of claim 28, wherein said locating step also includes disposing a plurality of tubes in fixed position about a second fabricated dental stent and along said defined plane of lateral inclination.

32. The method of claim 31, wherein said locating step further includes selectively passing a probe through each of said tubes for detecting the dental bone at various select locations.

33. The method of claim 31, wherein said placement directing step comprises disposing a guide member along the defined optimal plane of lateral inclination in a direction reflecting the defined optimal anterior/posterior inclination.

34. The method of claim 33, wherein said placement directing step further includes fabricating a third dental stent for carrying and selectively transferring said disposed guide member in fixed position between said dental cast and the patient's mouth.

35. The method of claim 34, wherein said placement directing step further includes the step of selectively receiving a drill through said guide member for directing said drill to the implant site when said guide member, carried by said third stent, is in said patient's mouth.

36. The method of claim 34, wherein said placement directing step further includes the step of selectively receiving through said guide member means for delivering said implant to said implant site when said guide member, carried by said third stent, is in said patient's mouth.

37. A method for accurately positioning a tooth implant in an implant site located along the alveolar ridge of a patient's mouth comprising:

producing a dental impression cast of said mouth;

defining an optimal plane of lateral inclination for placing said implant in said site in order to produce a planar surface of lateral inclination along said cast which reflects the defined plane;

determining dental bone location in said alveolar ridge adjacent where said implant site is located in order to record said bone location on said planar surface of lateral inclination produced along said dental cast;

defining an optimal anterior/posterior inclination along said planar surface of lateral inclination produced along said dental cast for placing said implant in said site by simulating a desired angle of anterior/posterior inclination along said planar surface of lateral inclination produced on said cast; and directing placement of said tooth implant in said implant site based on 1) said anterior/posterior inclination defined along said planar surface of lateral inclination and 2) the recorded bone location on said planar surface.

38. The method of claim 37, wherein said simulating step comprises rotatably fixing a pin along the planar surface of lateral inclination of the dental cast.

39. The method of claim 38, wherein said fixing step comprises fixing said pin along the planar surface of lateral inclination where said bone location was recorded thereon.

40. The method of claim 38, wherein said simulating step further includes the step of selectively rotating said pin about one end thereof in order to select the optimal anterior/posterior inclination.

* * * * *